United States Patent [19]

Hale

[11] 4,415,858

[45] Nov. 15, 1983

[54] PH METER PROBE ASSEMBLY

[75] Inventor: Charles J. Hale, San Jose, Calif.

[73] Assignee: The United States of America as represented by the U.S. Department of Energy, Washington, D.C.

[21] Appl. No.: 273,154

[22] Filed: Jun. 12, 1981

[51] Int. Cl.³ .............................................. G01N 27/56
[52] U.S. Cl. ..................................... 324/438; 210/793
[58] Field of Search ................ 324/438, 439; 210/793; 204/402, 409, 420

[56] References Cited

U.S. PATENT DOCUMENTS 2,209,487   7/1940   Wagner ............................. 324/438
4,187,175   2/1980   Roberts ............................. 210/793

*Primary Examiner*—Michael J. Tokar
*Attorney, Agent, or Firm*—L. E. Carnahan; Roger S. Gaither; Richard G. Besha

[57] ABSTRACT

An assembly for mounting a pH probe in a flowing solution, such as a sanitary sewer line, which prevents the sensitive glass portion of the probe from becoming coated with grease, oil, and other contaminants, whereby the probe gives reliable pH indication over an extended period of time. The pH probe assembly utilizes a special filter media and a timed back-rinse feature for flushing clear surface contaminants of the filter. The flushing liquid is of a known pH and is utilized to check performance of the probe.

13 Claims, 1 Drawing Figure

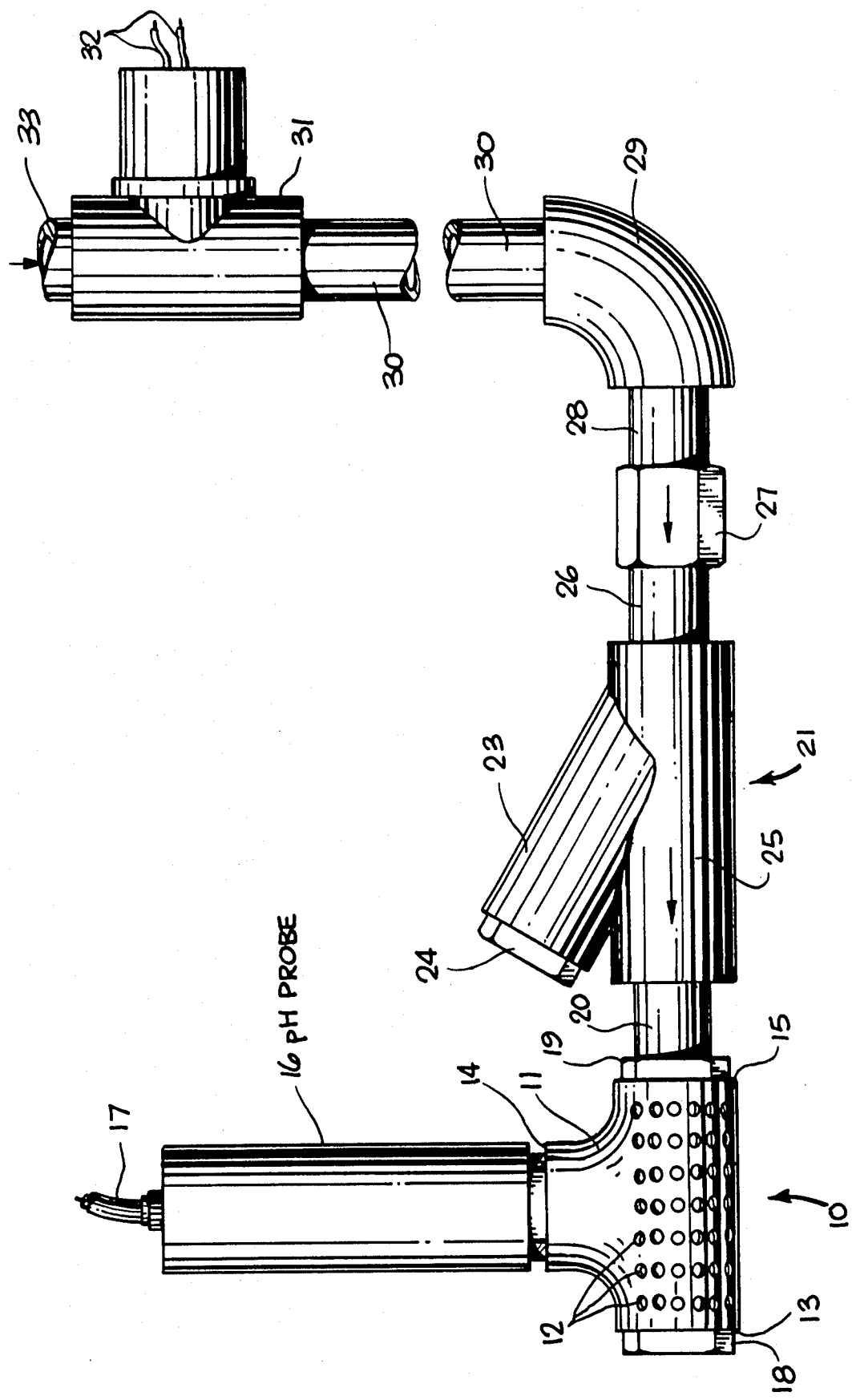

PH METER PROBE ASSEMBLY

The Government has rights in the invention described herein which arose at the Stanford Linear Accelerator Center in the course of, or under, Contract No. DE-AC03-76SF00515 between Stanford University and the U.S. Department of Energy.

BACKGROUND OF THE INVENTION

This invention relates to apparatus for measuring the pH of a solution, particularly for preventing contamination of the pH probe thereof, and more particularly to preventing contamination of the probe and providing means for flushing the probe which additionally serves to check that the probe is functional.

Environmental regulations require measuring the pH of solutions such as sanitary and storm sewer effluents. It is desirable to measure the pH right in the stream. Generally, such streams are loaded with contaminants such as oil, grease, paint, micro-organism growth, etc. Apparatus for measuring the pH of such streams utilize electrodes enclosed in a sensitive glass wherein hydrogen ions migrate through the glass pores, whereby a readout of the pH is provided. These glass-type pH probes provide quick response to changes in effluent pH. The probe glass becomes coated or fouled by the contaminants, whereby the hydrogen ions can no longer migrate through the glass. Thus, to provide effective pH monitoring, it is necessary to remove the coating on the glass caused by the contaminants.

Various schemes have been tried in an effort to prevent fouling of pH probes. For example, it has been proposed to provide a scrubbing or wiping mechanism which would remove the accumulation as it is collected on the probes. Attempts were also made at cleaning the probes by high-flow velocities, ultrasonic cleaning, and also by periodically cleaning with steam. Also, filtering of the solution prior to contact with the probe has been utilized. The schemes have proved to be ineffective and, in many instances, require a substantial amount of down-time of the monitoring system, as well as costs of the cleaning arrangements. In addition, many probes must be recalibrated whenever cleaned or removed for cleaning, thus causing continuous monitoring and calibration by technical personnel. These prior approaches are exemplified by the following:

U.S. Pat. No. 3,290,584, issued Dec. 6, 1966, to Van Dewisen Harms et al., discloses a pH probe mounting assembly incorporating a filter means. Liquid enters an overflow chamber and passes through a sheet of filter paper prior to its entering a pH probe containing c chamber. The filter paper is continuously rolled so that a fresh portion of paper continuously filters the liquid.

U.S. Pat. No. 3,440,525, issued Apr. 22, 1969, to C. P. Cardeiro, discloses a pH-sensitive electrode that minimizes errors due to drifts by providing a substantial excess of undissolved salt crystals immersed in a saturated salt bridge solution communicable, by numerous capillaries, between chambers, one of which contains the test solution.

U.S. Pat. No. 4,151,255, issued Apr. 24, 1979, to I. A. Capuano et al. discloses an apparatus for measuring the pH of a sample. The apparatus has a rinse and buffer standardization system and is used to automatically and periodically standardize the pH measuring means.

Thus, a need exists to prevent the current rapid contamination of pH probes and for reducing the time period for the required periodic checking of the function of such probes. Further, there is a need for a pH probe assembly that can be inserted directly into a contaminated stream.

SUMMARY OF THE INVENTION

It is an object of this invention to provide an improved pH probe assembly.

A further object of the invention is to provide a pH probe assembly which includes means for preventing contamination thereof due to contaminants in the liquid being monitored.

A still further object of the invention is to provide a filter arrangement for a pH probe which substantially increases reliability and operational time of the probe.

Another object of the invention is to provide a pH probe meter assembly for effluents such as that flowing in sanitary and storm sewers, which utilizes a filter and flushing arrangement to maintain reliable pH indication over an extended period of time.

Another object of the invention is to provide a pH probe filter arrangement with a flushing means which can be utilized to check the function of the probe.

Other objects of the invention will become apparent from the following description and accompanying drawings.

The invention is a pH probe assembly with a special filter media which excludes oil, grease, paint and other contaminants over a reasonable time. The filter media allows liquid effluent clear of foulants to pass through to the pH probe. A timed back-rinse feature is incorporated which gives the filter media longer life by flushing clear surface contaminants. The liquid used for flushing can be varied to handle the type of conamination in a variety of applications. A flushing liquid of known pH can be used to check performance of the probe as determined by the pH instrument.

More specifically, the invention involves a pH meter assembly having a pH probe located in a filter media through which the effluent being monitored passes, and means for flushing the filter media for removing surface contaminants therefrom, the flushing means including a timing mechanism, a strainer, and a check valve which is connected to a source of selected flushing fluid.

BRIEF DESCRIPTION OF THE DRAWING

The single FIGURE illustrates an embodiment of a pH meter probe assembly in accordance with the invention.

DETAILED DESCRIPTION OF THE INVENTION

The present invention is a pH meter probe assembly for measuring the pH in effluents, such as in sanitary and storm sewers. In the probe assembly of the invention, the pH probe is mounted in an apertured member containing filter media to prevent contamination of the probe, and a rinse or flush mechanism is connected to the apertured member for flushing contaminant from the surface of the filter media. The flush mechanism utilizes a liquid of known pH which is used to check performance of the pH probe.

As pointed out above, composition of sanitary and storm sewer effluents are monitored by measuring the pH thereof. Glass-type pH probes are highly desirable for this type of monitoring because of their quick response to changes in effluent pH. Streams of effluents are loaded with contaminants such as oil, grease, paint, micro-organism growth, etc., which coat or foul the sensitive glass component of pH probes, thus resulting in very short life of such probes without cleaning.

The present invention houses the glass-type pH probe within a filter media and protects it from contaminants so that it can function over an extended period of time when inserted directly into a flowing stream of contaminated effluent. The contaminants are filtered out of the effluent and allows effluent clear or foulant admitted to the probe, thus allowing the glass to function normally. A timed back rinse or flush gives the filter media longer life by flushing clear surface contaminants from the filter media. The liquid used for flushing can be varied to handle the type of contamination in a variety of applications, and be used to check performance of the probe.

The pH probe assembly of the invention can be used in a wide variety of applications by choosing the proper filter media and the type of flushing liquid used. The probe assembly, for more efficient operation, should be inserted in a flowing stream. This can be accomplished, if the effluent is not flowing (as in plating-shop tanks), by pumping the effluent across the perforated probe holder containing the filter media. While the probe assembly is particularly applicable for pH monitoring of sanitary and storm sewer lines, it can be effectively utilized in a variety of other applications such as around steel pickling plants, in cooling tower blow-down streams, etc.

Referring now to the embodiment of the invention illustrated in the drawing, the pH meter assembly comprises a glass-type probe assembly 10 consisting of a T-shaped member or housing 11 having a plurality of perforation or apertures 12 provided with three (3) openings 13, 14 and 15, with a pH probe 16 secured in opening 14 and provided with a coaxial cable 17 for connection to a pH instrument, as known in the art. The operation of the pH probe 16 and its associated pH instrument, not shown, is known in the art as illustrated by the above-referenced prior art, and thus description thereof is deemed unnecessary. Opening 13 of T-shaped member 11 is closed by a plug 18 while opening 15 is connected via a coupling 19 and pipe 20 to a strainer assembly 21 to prevent the filter media from moving away from the probe 16. Perforated member 11, pipe 20 and an adjoining section 22 of strainer assembly 21, are filled with a selected filter media such as filtration grade coarse sand. Strainer assembly 21 is provided with a section 23 having a plug 24 therein and a section 25 which is secured via a pipe 26 to a check valve 27. Check valve 17 is set at a pressure high enough to prevent backstreaming, but at a pressure low enough to allow the flushing liquid to be pumped through the housing 11. Check valve 27 is secured via a pipe 28, elbow 29 and pipe 30 to a time-operated solenoid valve assembly 31, connected electrically to a power source and time via leads 32. Valve assembly 31 is connected via a pipe 33 to a source, not shown, of back-rinse or flushing fluid or liquid, such as domestic water. The purpose of the timer-controlled solenoid valve is to admit the flushing liquid to purge the entire probe assembly at predetermined intervals. The type of flushing liquid is determined on the basis of the contamination which fouls the filter media.

In operation, probe assembly 10 is immersed into the effluent to be sampled to allow flow of the effluent through the perforations 12 to the probe 16. Periodically, the filter media in housing 11 is flushed by activation of the time-operated solenoid valve assembly 31, thereby substantially increasing the operational time of the probe without removal for cleaning.

By way of example, housing 11 may be a ¾-inch plumbing T constructed of stainless steel or bronze, with 100 apertures 12 of 0.050-inch diameter. Strainer assembly 21 may be constructed of stainless steel or bronze, with check valve 27 being made of stainless steel or bronze, and an operating back pressure above the pressure head of the system in which probe is installed. Elbow 29 is of the ⅜-inch type made of stainless steel or bronze with pipes 20, 26, 28, 30 and 33 being ⅜ inch made of stainless steel or bronze. Solenoid valve assembly 31 is operatively connected to a power supply, now shown, and operates on low current with a supply voltage of 24 volts DC to 120 volts AC. The overall length from housing 11 to elbow 29 is 12–13 inches, for example. The type of flushing liquid and the time sequence for flushing the filter media is dependent on the type of media and contaminants, but with coarse water treatment grade glacial granite sand as the media and with grease or oil as the contaminant, the flushing liquid would be water of known pH and the time sequence of flushing is 15 sec. to 60 sec. Other types of filter media includes detergent solutions and acid solutions, or whatever is necessary to remove the contaminant.

By selecting a flushing fluid of a known pH, the operation and calibration of the probe and the pH instrument are checked each time the probe assembly is flushed. A glass-cleaning solution may be run through on a separate line periodically to also clean the pH probe glass.

The present invention allows a pH probe to function over an extended period of time without the need for techniques to remove the probe, clean, calibrate and reinstall it. Thus, the costs of pH monitoring are substantially decreased. By installing the invention in a turbulent stream and using the proper flushing liquid, it will continue to function over long periods of time. For example, the normal time period of a pH probe in contaminants exemplified above is about 4 hours, while the time period when using the invention is increased to about 160 hours or more.

While a particular embodiment of the invention has been illustrated and described, modifications will become apparent, and it is intended to cover in the appended claims all such modifications as come within the scope of the invention.

What is claimed is:

1. A pH probe assembly for measuring the pH in effluents, such as in sanitary and storm sewers, said assembly comprising a perforated housing having a pH probe mounted therein and containing a filter media which surrounds at least a portion of said pH probe for preventing contamination of said pH probe, and means connected to said perforated housing for periodically flushing said filter media for removing contaminants therefrom.

2. The pH probe assembly of claim 1, wherein said perforated housing is of a T-shaped configuration, said pH probe being mounted in a first leg of said T-shaped housing, and said flushing means being operatively connected to a second leg of said T-shaped housing.

3. The pH probe assembly of claim 2, wherein a third leg of said T-shaped housing is plugged.

4. The pH probe of claim 1, wherein said flushing means includes a time-controlled valve arrangement.

5. The pH probe assembly of claim 4, wherein said flushing means additionally includes a strainer assembly and a check valve positioned in series arrangement between said perforated housing and said time-controlled valve arrangement.

6. The pH probe assembly of claim 5, wherein said time-controlled valve arrangement includes a solenoid-actuated valve for allowing an associated supply of flushing liquid to pass through said check valve, through said strainer assembly and through said perforated housing for removing contaminants from said filter media.

7. The pH probe assembly of claim 6, wherein said perforated housing, said strainer assembly, and said check valve are positioned in axial alignment, and wherein said solenoid-actuated valve is operatively connected to said check valve so as to be on an axis substantially perpendicular to said axial alignment.

8. The pH probe assembly of claim 1, wherein said filter media consists of coarse water treatment grade glacial granite sand, and wherein said flushing means utilizes a flushing liquid selected from the group consisting of water, detergent solutions, and acid solutions.

9. The pH probe assembly of claim 1, wherein said pH probe includes a glass member located within said filter media.

10. A method for increasing the operating time by preventing contamination of a pH probe by contaminants in a fluid being monitored by the pH probe, comprising the steps of: surrounding at least a portion of said pH probe with a filter media, and periodically flushing the filter media with a fluid for removing contaminants thereon.

11. The method of claim 10, wherein the step of surrounding the pH probe with filter media is carried out by positioning the probe in a perforated housing containing the filter media, and wherein the step of periodically flushing the filter media is carried out by connecting a time-controlled means to the perforated housing for periodically directing the flushing fluid through the perforated housing for removing contaminants from the filter media contained therein.

12. The method of claim 11, additionally including the step of: positioning strainer means intermediate the perforated housing and the time-controlled means for preventing the filter media from moving away from the pH probe toward the time-controlled means.

13. The method of claim 11, additionally including the step of: positioning a check valve intermediate the perforated housing and the time-controlled means for preventing backstreaming of liquid from the perforated housing toward the time-controlled means.

* * * * *